United States Patent [19]
Markland, Jr. et al.

[11] Patent Number: 5,731,288
[45] Date of Patent: Mar. 24, 1998

[54] COMPOSITIONS CONTAINING CONTORTROSTATIN AND METHODS FOR THE USE THEREOF

[75] Inventors: Francis S. Markland, Jr., Northridge, Calif.; Benedict R. Lucchesi, Ann Arbor, Mich.; Mohit Trikha, Los Angeles, Calif.

[73] Assignee: University of Southern California, Los Angeles, Calif.

[21] Appl. No.: 632,691

[22] Filed: Apr. 15, 1996

Related U.S. Application Data

[62] Division of Ser. No. 540,423, Oct. 10, 1995, abandoned, which is a continuation of Ser. No. 141,321, Oct. 22, 1993, abandoned.

[51] Int. Cl.$^6$ ............................. A61K 38/16; C07K 14/00
[52] U.S. Cl. .............................................. 514/12; 530/324
[58] Field of Search ............................... 514/12; 530/324

[56] References Cited

U.S. PATENT DOCUMENTS

| | | | |
|---|---|---|---|
| 4,610,879 | 9/1986 | Markland, Jr. et al. | 424/94.67 |
| 5,066,592 | 11/1991 | Huang et al. | 514/12 |
| 5,182,260 | 1/1993 | Maraganore et al. | 514/12 |
| 5,196,403 | 3/1993 | Maraganore et al. | 514/12 |

OTHER PUBLICATIONS

Chao et al. "Agkistrodon piscivorus piiscivorus Platlet Aggregation Inhibitor: A Potent Inhibitor of Platelet Activation", *Proc. Natl. Acad. Sci USA*, vol. 86, pp. 8050–8054, Oct. 1989.
Clark, Richard A.F., "Potential Roles of Fibronectin in Cutaneous Wound Repair", *Arch. Dermatol.*, vol. 124, Feb., 1988.
Coller et al., "A Murine Monoclonal Antibody That Completely Blocks the Binding of Fibrinogen to Platelets Produces a Thrombasthenic–like State in Normal Platelets and Binds to Glycoproteins IIb and/or IIIa", *J. Clin. Invest.*, vol. 72, pp. 325–338, Jul. 1983.
Connolly, T.M. et al., "The Snake Venom Protein s–Echistatin Inhibits Platelet Adhesion to Collagen by both RGD–Dependent and Independent Mechanism", *Circulation*, vol. 82 (Suppl. III), pp. 660 (1990).
Dennis et al., "Platelet Glycoprotein IIb–IIIa Protein Antagonists from Snake Venoms: Evidence for a Family of Platelet–Aggregation Inhibitors", *Proc. Natl. Acad. Sci. USA*, vol. 87, pp. 2471–2475, Apr. 1989.
diZerega, Gere S., "The Cause and Prevision of Postsurgical Adhesions: A Contempory Update", *Gynecologic Surgery and Adhesion Prevention*, pp. 1–18 (Wiley–Liss, Inc. 1993).
Gan et al., "Echistatin", *J. Biol. Chem.*, vol. 263, pp. 19827–29832 (1988).
Ginsberg et al., "Cytoadhesins, Integrins, and Platelets", *Thrombos. Haemostas.*, vol. 59, pp. 1–5 (1988).
Grinnell, Frederick, "Fibronectin and Wound Healing", *J. of Cellular Biochem.*, vol. 26, pp. 107–116 (1984).

Holahan et al., "Prevention of Reocclusion following Tissue Type Plasminogen Activator–Induced Thrombolysis by the RGD–Containing Peptide. Echistatin, in a Canine Model of Coronary Thrombosis", *Pharmacology*, vol. 42, pp. 340–348 (1991).
Huang et al., "Trigramin", *J. Biol. Chem.*, vol. 262, pp. 16157–16163 (1987).
Hynes, Richard O., "The Compolexity of Platelet Adhesion to Extracellualr Matrices", *Thrombosis and Haemostasis*, vol. 66, pp. 40–43 (1991).
Rodgers et al., "Intraperitoneal Tolmetin Prevents Postsurgical Adhesion Formation in Rabbits", *Int. J. Fertil.*, vol. 35, pp. 40–45 (1990).
Romson et al., "Electrical Induction of Coronary Artery Thrombosis in the Ambulatory Canine: A Model For In Vivo valuation of Anti–thrombotic Agents", *Thrombosis Research*, vol. 17, pp. 841–853 (1980).
Sato et al., "Echistatin Is a Potent Inhibitor of Bone Resorption in Culture", *J. Cell Biol.*, vol. 111, pp. 1713–1723 (1990).
Savage, et al., "Binding of the Snake Venom–derived Proteins Applaggin and Echistatin to the Arginine–Glycine–Aspartic Acid Recognition Site(s) on Platelet Glycoprotein IIb–IIIa Complex Inhibits Receptor Function", *J. Biol. Chem.*, vol. 265, pp. 11766–11772 (1990).
Scarborough et al., "Barbourin", *J. Biol. Chem.*, vol. 266, pp. 9359–9362 (1991).
Shebuski et al., "Acceleration of Recombinant Tisue–Type Plasminogen Activator–Induced Thrombolysis and Prevention of Reocclusion by the Combination of Heparin and the Arg–Gly–Asp–Containing Peptide Bististatin in a Canine Model of Coronary Thrombosis", *Circulation*, vol. 82, pp. 169–177 (1990).
Sible, J.C. & Oliver, N., "Fibronectin Expression in Keloids", *J. Cell. Biochem. Suppl.*, vol. 16F, pp. 170 (1992).
Trikha et al., "Characterization of a Novel Platelet Aggregation Inhibitor (Contortrostatin) From the Southern Copperhead Snake Venom", *Blood*, vol. 76, No. 10, Suppl. 1, pp. 479a (Nov. 15, 1990).
Trikha et al., "A Novel Platelett Aggregation Inhibitor from Southern Copperhead Snake Venom", *Fibrinolysis*, vol. 4, Suppl. 1, pp. 105 (1990).
Trikha et al., "Inhibition of Tumor Cell Binding to Fibronectin in the Presence of Sanke Venom Disintegrins", *Proceedings of the Amer. Assoc. for Cancer Res.*, vol. 33, pp. 34 (1992).
Trikha et al., "Purification and Characterization of Three Platelet Aggregation Inhibitors", *J. Cellular Biochem.*, vol. 16F, pp. 180 (1992).

(List continued on next page.)

*Primary Examiner*—Cecilia J. Tsang
*Assistant Examiner*—Anish Gupta
*Attorney, Agent, or Firm*—Robbins, Berliner & Carson LLP

[57] ABSTRACT

Contortrostatin is employed as active agent for treatment of thrombotic disease. Preferably, contortrostatin is employed in conjunction with at least one thrombolytic agent. In addition, contortrostatin is useful in compositions and methods for preventing metastases in carcinoma and melanoma patients, treating or preventing osteoporosis and promoting wound healing.

8 Claims, 4 Drawing Sheets

OTHER PUBLICATIONS

Wencel–Drake et al., "Arg–Gly–Asp–Dependent Occupancy of GPIIb/IIIa by Applaggin: Evidence for Internalization and Cycling of a Platelet Integrin", *Blood*, vol. 81, pp. 62–69 (1993).

Yasuda et al., "Kistrin, a Polypeptide Platelet GPIIb/IIIa Receptor Antagonist, Enhances and Sustains Coronary Arterial Thrombolysis With Recombinant Tissue–Type Plasminogen Activator in a Canine Preparation", *Circulation*, vol. 83, pp. 1038–1047 (1991).

Yasuda et al., "Comparative Effects of Aspirin, a Synthetic Thrombin Inhibitor and a Monoclonal Antiplatelet Glycoprotein IIb/IIIa Antibody on Coronary Artery Reperfusion, Reocclusion and Bleeding with Recombinant Tissue–Type Plasminogen Activator in a Canine Preparation", *J. Am. Coll. Cardiol.*, vol. 16, pp. 714–722 (1990).

Zucker, Majorie B., "The Fuctioning of Blood Platelets", *Sci. American*, vol. 242, pp. 86–103 (1990).

COMPOSITIONS CONTAINING CONTORTROSTATIN AND METHODS FOR THE USE THEREOF

This is a file wrapper divisional of U.S. patent application Ser. No. 08/540,423, filed Oct. 10, 1995, now abandoned, which in turn is a continuation of U.S. patent application Ser. No. 08/141,321, filed Oct. 22, 1993, now abandoned.

BACKGROUND OF THE INVENTION

The present invention relates generally to the fields of biochemistry and medicine. In particular, the present invention is directed to compositions and methods for use in treating thrombotic disease, including thrombosis and thromboembolism.

Platelets serve an important role in mediating coronary artery thrombosis and rethrombosis in the genesis of acute myocardial infarction [Zucker, M. B., *Sci. American* 242:86 (1990)]. Thus, inhibition of platelet aggregation may provide an effective adjunctive approach for prevention of coronary artery reocclusion after successful thrombolytic therapy.

Platelet aggregation involves the interaction of the platelet membrane glycoprotein (GP) IIb/IIIa receptor with plasma fibrinogen. GPIIb/IIIa belongs to the superfamily of integrin cell surface receptors [Hynes, R. O., *Thrombos. Haemostas.* 66:40 (1991)]. Integrins are heterodimers composed of $\alpha$ and $\beta$ subunits that are non-covalently associated. They have been shown to be involved in cell-cell and cell-substratum interactions. Both the $\alpha$ and the $\beta$ subunits are required for fibrinogen binding. Integrins serve as receptors for extracellular matrix proteins such as fibronectin, fibrinogen, vitronectin, collagen and laminin. Some of these interactions have been shown to be mediated via an Arg-Gly-Asp (RGD) sequence present in the matrix proteins. For platelet aggregation an RGD sequence present in fibrinogen is essential for the interaction with GPIIb/IIIa [Ginsberg, M. H. et al., *Thrombos. Haemostas.* 59:1 (1988)].

A number of proteins purified from venom of snakes of the Crotalidae and Viperidae families have been found to inhibit glycoprotein (GP) IIb/IIIa mediated platelet aggregation [see, e.g., Huang, T. F. et al., *J. Biol. Chem.* 262:16157 (1987); Gan, Z. R. et al., *J. Biol. Chem.* 263:19827 (1988); Yasuda, T. et al., *J. Am. Coll. Cardiol.* 16:714 (1990); Trikha, M. et al., *Fibrinolysis* 4 (Suppl. 1):105 (1990); Trikha, M. et al., *Blood* 76 (Suppl. 1):479a (1990); Holahan, M. A. et al., *Pharmacology* 42:340 (1991); Shebuski, R. J. et al., *Circulation* 82:169 (1990); Yasuda, T. et al., *Circulation* 83:1038 (1991)]. These proteins, classified as disintegrins, are typically disulfide rich. Moreover, all disintegrins isolated thus far, with the exception of barbourin [Scarborough, R. M. et al., *J. Biol. Chem.* 266:9359 (1991)] contain an RGD (Arg-Gly-Asp) sequence that has been implicated as being involved in the inhibition of integrin-mediated interactions. In particular, the RGD sequence of the disintegrins may compete for fibrinogen binding sites of the platelet membrane, thereby inhibiting platelet aggregation induced by ADP or other agents.

Nonetheless, there appears to be increasing evidence that disintegrins may have unique surface geometry which facilitates interactions with integrins by mechanisms other than those based solely upon the RGD site. For example, the finding that a mutated, chemically synthesized derivative of echistatin (in which alanine was substituted for arginine in the RGD sequence) still possessed some biological activity, suggests that other regions in the protein may be involved in binding and that there may be some flexibility in the RGD binding site [Connolly, T. M. et al., *Circulation* 82 (Suppl. III):660 (1990)]. Synthetic RGD peptides, due to their small size, generally do not possess the molecular topography of the disintegrins and therefore cannot interact via the multiplicity of mechanisms likely to be involved in disintegrin binding.

Prevention of reocclusion following thrombolysis using tissue-type plasminogen activator in a canine model system has been reported using 30 µg/kg plus 3 µg/kg/min bitistatin, an 83 amino acid disintegrin derived from the venom of *Bitis arietans* [Shebuski et al., supra] and 15 µg/kg/min i.v. echistatin, a 49 amino acid disintegrin derived from the venom of *Echis carinatus* [Holahan et al., supra]. In the reported methods, an initial bolus of heparin (100 U/kg i.v.) and subsequent hourly boluses of 50 U/kg were used to increase activated partial thromboplastin times at least 1.5-fold over the control. Whereas it had previously been observed that heparin in combination with tissue-type plasminogen activator (tPA) did not affect the incidence of acute reocclusion in this model system, the addition of echistatin or bistatin lead to dramatic reductions in the incidence of acute thrombotic reocclusion. The administration of heparin was, however, apparently necessary for prevention of acute thrombotic reocclusion.

Similarly, kistrin (a 68 amino acid disintegrin derived from the venom of *Agkistrodon rhodostoma*) was evaluated in conjunction with recombinant tissue-type plasminogen activator in a canine model of coronary artery thrombosis with superimposed high grade stenosis [Yasuda et al. (1991), supra]. An effective dose of 4 µg/kg/min was determined to be sufficient to prevent reocclusion. Simultaneous systemic therapeutic heparin anticoagulation was used; the dose of heparin was selected to maintain the activated partial thromboplastin time more than two-fold throughout the experimental observation period.

U.S. Pat. No. 5,066,592 to Huang et al. describes the use of trigramin, a 72 amino acid disintegrin isolated from the venom of *Trimeresurus gramineus*, to inhibit fibrinogen binding to human platelets and thereby to inhibit fibrinogen-induced aggregation of human platelets. Trigamin is also reported to inhibit binding of von Willebrand factor to platelets. Trigamin is reported to inhibit $^{125}$I-fibrinogen binding to ADP (10µ molar)-stimulated platelets in a concentration-dependent manner with an $IC_{50}$ of 2.8–5.6× $10^{-8}$M.

Isolation of an anti-platelet factor applaggin from the venom of *Agkistrodon piscivorus piscivorus* has also been reported [Chao, B. H. et al., *Proc. Natl. Acad. Sci. USA* 86:8050 (1989); Savage, B. et al., *J. Biol. Chem.* 265:11766 (1990)]. Applaggin, unlike trigramin, is reported to inhibit dense-granule secretion in concert with inhibition of platelet aggregation in a dose-dependent manner. While initially described as a homodimer with at least two interchain disulfide bridges [Chao et al. (1989), supra], a subsequent report indicated that analysis of purified applaggin by mass spectroscopy showed the presence of applaggin monomers with a mass of 7,666 Daltons and no evidence of dimerization [Wencel-Drake, J. D. et al., *Blood* 81:62 (1993)].

One disintegrin of particular interest is contortrostatin, which has been isolated from the venom of *Agkistrodon contortrix contortrix* (the southern copperhead snake). The originally-reported purification procedure included molecular sieve chromatography on Sephadex G-100 SF, desalting on Sephadex G-25F and reverse phase HPLC. ADP-enhanced aggregation of stirred human platelet rich plasma and the inhibition thereof by contortrostatin were monitored at 37° C. It was found that preincubation for 1 minute of the platelet rich plasma ($3 \times 10^5/mm^3$) with 5 μl of the low molecular weight peak after Sephadex G-100 SF resulted in 76% inhibition of platelet aggregation induced by 10 μM ADP [Trikha et al. (1990), supra].

In a subsequent report it was noted that in crude venom, the inhibitor was not readily detectable due to the presence of platelet aggregating activity; however, following the first step of purification (hydrophobic interaction HPLC) inhibitory activity was separated from both aggregating activity and an α-chain degrading fibrinolytic enzyme present in the venom. Inhibitory activity was pooled following HPLC and applied to a hydroxylapatite HPLC column. In the final step of purification, $C_4$ reverse phase HPLC chromatography was employed. The yield of the homogeneous protein was 3–5 mg per gram of venom. Contortrostatin was reported to have a molecular weight of 18–21 kD under non-reducing conditions and 9 kD under reducing conditions; thus, the molecule was believed to be a homodimer with the two subunits being held together by disulfide bond(s). Isoelectric focusing showed that the protein had an acidic pI. Contortrostatin was reported not to exhibit fibrinolytic activity and was not a 5'-nucleotidase or a phospholipase based on molecular size and kinetics of inhibition of platelet aggregation. Following preincubation for 1 minute, contortrostatin at approximately 100 nM was reported to completely inhibit ADP-induced platelet aggregation [Trikha et al. (1990), supra].

It has further been reported that contortrostatin has 70 amino acids with five to six disulfide bridges, and that the sequence of contortrostatin appears to begin 10 amino acids downstream of applaggin (a platelet aggregation inhibitor from the venom of *Agkistrodon piscivorus piscivorus*). It was speculated that contortrostatin may have an insertion and/or a C-terminal extension of nine amino acids. It was further reported that a 50% inhibition ($IC_{50}$) of human platelet aggregation in platelet rich plasma was observed at 0.8 μg/ml of contortrostatin, and at 2.2 μg/ml with canine platelets [Trikha, M. et al., *Journal of Cellular Biochem.* 16F:180 (1992)].

Contortrostatin was reported to inhibit binding of human fibrosarcoma (HT-1080) and c-Ha-ras transfected rat embryo (4R) cells to fibronectin coated plates but not to matrigel coated plates. Inhibition of 4R cell binding to fibronectin in the presence of contortrostatin at 1 μg/ml and 5 μg/ml was 46% and 88%, respectively, and for HT1080 cells inhibition was 89% and 85%, respectively [Trikha, M. et al., *Proceedings of the American Association for Cancer Research* 33:34 (1992)].

It is an object of the present invention to provide compositions and methods useful in the prevention and treatment of a variety of conditions, including but not limited to thrombotic disease.

SUMMARY OF THE INVENTION

In accordance with the present invention, the unique properties of contortrostatin are exploited in methods and compositions for treatment of a variety of different conditions. Pursuant to a first embodiment of the present invention, compositions and methods employing contortrostatin as active agent are provided for treatment of thrombotic disease. In a preferred aspect of this first embodiment, contortrostatin is employed in conjunction with at least one thrombolytic agent. Pursuant to other embodiments of the present invention, contortrostatin is employed in compositions and methods for preventing metastases in carcinoma and melanoma patients, treating or preventing osteoporosis and promoting wound healing.

BRIEF DESCRIPTION OF THE DRAWINGS

The invention may be better understood with reference to the accompanying drawings, in which.

DETAILED DESCRIPTION OF THE INVENTION

Figure 1:
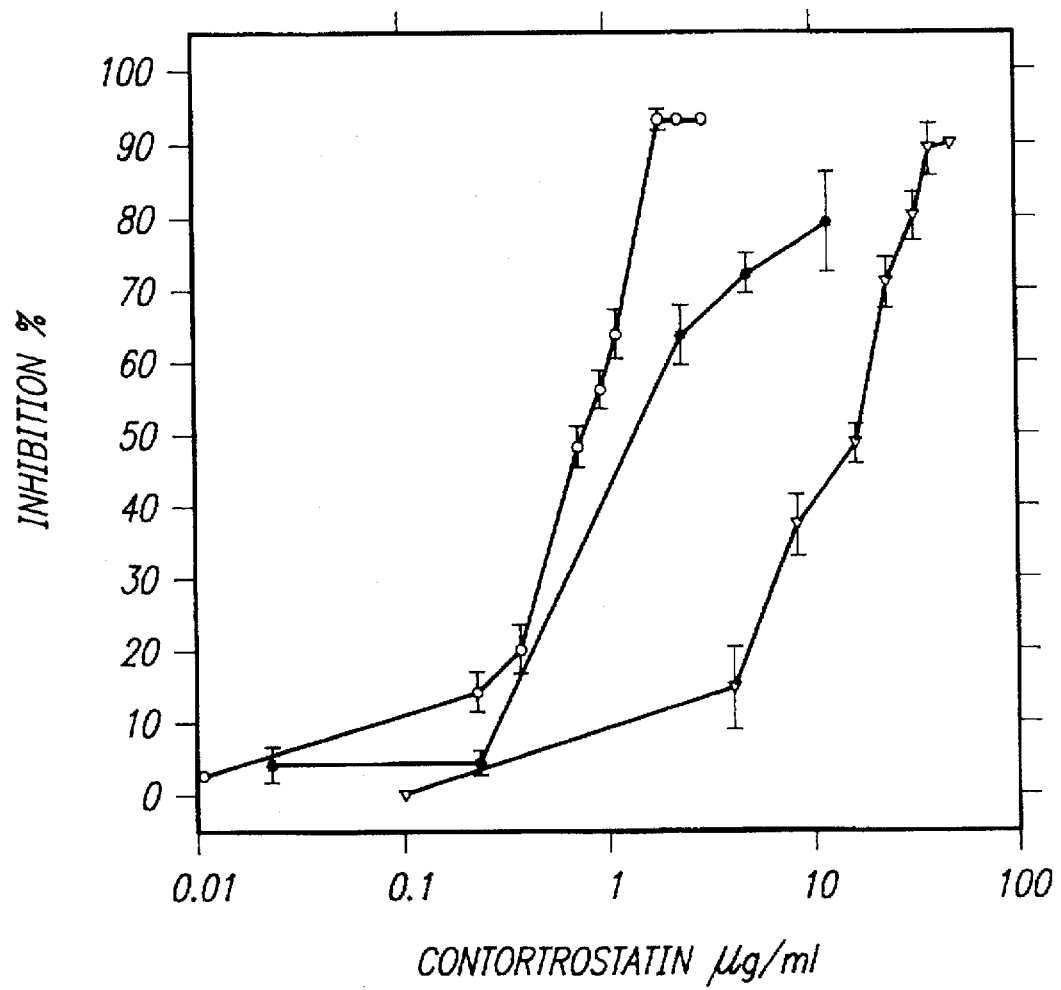
FIG. 1 illustrates the results of determinations of contortrostatin inhibition of human, canine and rabbit platelet aggregation.

Contortrostatin has been characterized as a dimer comprising 70 amino acids in each chain with 10 to 12 half-cystine units. The amino acid sequence for a portion of the contortrostatin molecule has been determined as follows (with "Xaa" indicating the locations of amino acids not yet positively identified):

Asp—Pro—Glu—Asn—Pro—Cys—Cys—
Asp—Ala—Thr—Cys—Lys—Leu—Arg—
Thr—Gly—Ser—Gln—Cys—Ala—Glu—
Gly—Leu—Cys—Xaa—Asp—Gln—Cys—
Xaa—Phe—Met—Lys—Glu—Cys—
Gly—Glu—Gly—Gly—Xaa—Val—Xaa—
Xaa—Gly—Asp—Xaa [SEQ ID NO:1].

This partial amino acid sequence of contortrostatin shows significant identity with that reported for applaggin [Chao et al. (1989), supra; U.S. Pat. Nos. 5,182,260 and 5,196,403 to Maraganore et al.]. However, the sequence for contortrostatin begins nine amino acid residues downstream from the applaggin start site. Presumably, the amino terminal deletion has no effect on disintegrin activity, as the $IC_{50}$ values for contortrostatin and applaggin are very similar.

Contortrostatin is clearly quite different from applaggin, as the latter has be demonstrated unmistakably to be a monomer [Wencel-Drake et al. (1993), supra]. Moreover, contortrostatin does not inhibit platelet release reactions, as has been demonstrated to be the case with applaggin in the aforementioned U.S. Pat. Nos. 5,182,260 and 5,196,403 to Maraganore et al. Finally, despite the similarities in sequence there are also significant differences between the sequences with respect to both the start site and the presumed insertion at the carboxyl-terminal end of contortrostatin.

Contortrostatin has been found to be a potent inhibitor of human, rabbit and canine platelet aggregation in vitro. Unlike applaggin, however, contortrostatin does not inhibit platelet release reactions. Platelet comprise a plurality of different granules, including alpha granules and dense granules, whose contents are released when the platelets aggregate. The finding that contortrostatin does not inhibit platelet release of granule contents (including ATP from the dense granules) signifies that the platelets may still release their contents (and thus maintain some semblance of normal physiological activity) notwithstanding the inhibition of aggregation. By contrast, when applaggin inhibits platelet aggregation it also inhibits platelet release (as measured by, e.g., inhibition of serotonin release from the dense granules). Thus, normal platelet physiological processes are necessarily further perturbed with administration of applaggin.

Several lines of evidence indicate that contortrostatin inhibits platelet aggregation by binding specifically to the GPIIb/IIIa integrin receptor. For example, in a fibrinogen-GPIIb/IIIa ELISA [Dennis, M. S. et al., Proc. Natl. Acad. Sci. (USA) 87:2471 (1990)], in which the extent of purified GPIIb/IIIa bound to immobilized fibrinogen can be quantitated, contortrostatin effectively blocks GPIIb/IIIa binding. Additionally, the partial amino acid sequence of contortrostatin indicates considerable similarity with other disintegrins known to bind to GPIIb/IIIa. Finally, contortrostatin blocks 7E3 binding to GPIIb/IIIa. 7E3 is a murine monoclonal antibody that specifically binds to GPIIb/IIIa, thereby inhibiting human and canine platelet aggregation [Coller, B. S. et al., J. Clin. Invest. 72:325 (1983)]. In the presence of a low concentration of contortrostatin, 7E3 binding to platelets is significantly inhibited.

Three snake venom disintegrins, kistrin [Yasuda et al. (1990), supra], echistatin [Holahan et al. (1991), supra] and bitistatin [Shebuski, R. J. et al. (1990), supra], have demonstrated a potential role as antithrombotic agents for use in thrombolytic therapy by enhancing and sustaining arterial thrombolysis in conjunction with recombinant tissue plasminogen activator. Based on the low $IC_{50}$ values of contortrostatin, its in vivo efficacy as an antithrombotic agent has been examined. Using a canine reoccluding carotid arterial thrombosis model, contortrostatin has been found to efficiently sustain opening of the carotid artery in conjunction with anisoylated plasminogen streptokinase activator complex (APSAC). APSAC alone was found insufficient to prevent the rapid reocclusion of the carotid artery. Heparin was not needed to sustain opening when contortrostatin was administered with APSAC. This is a significant distinction over other disintegrins (e.g., echistatin, bitistatin and kistrin) which have been evaluated in models of coronary artery thrombosis.

The compositions of the present invention are particularly useful for treatment of thrombotic diseases in mammals, alone or in conjunction with one or more thrombolytic agents. In particular, the compositions of the present invention have utility in treating or preventing arterial, venous and microvascular thrombosis and thromboembolism. Thus, the compositions have utility in treating stroke, transient ischemic attacks, arteriosclerosis, atherosclerosis, pulmonary embolism, aneurisms and angina. In particular, the compositions have utility in preventing or treating myocardial infarctions.

The compositions of the present invention also have utility in inhibiting metastases in melanoma and carcinoma patients. Contortrostatin has been observed to bind to at least two sites on human melanoma M24met cells: a high affinity site with a dissociation constant (Kd) of 1.1 (±0.7) nM and 96,000 (±39,000) sites per cell; and a lower affinity site with a Kd of 41 (±13) nM and 480,000 (±90,000) sites per cell. Moreover, contortrostatin has been found to inhibit human melanoma M24met cell adhesion to fibronectin and vitronectin, and to a lesser extent to collagen and laminin. Thus, methods and compositions for preventing metastases in melanoma and carcinoma patients is also contemplated as within the scope of the present invention.

The disintegrin-containing compositions of the present invention are also useful in treatment of osteoporosis. Osteoclasts are multinucleated cells up to 400 μm in diameter which resorb mineralized tissue in vertebrates. Bone resorption appears to proceed by a combination of processes involving attachment to bone, polarized secretion of acid and proteases, and active motility of osteoclasts along the bone substrate; osteoclasts bind to bone via an RGD-sequence as an obligatory step in bone resorption, and this RGD-binding integrin is at adhesion structures [Sato, M. et al., J. Cell Biol. 111:1713 (1990)]. The molecular mechanisms whereby osteoclasts attach to bone are not well understood; however, by analogy to other cells, members of the integrin superfamily of divalent cation-dependent adhesion molecules are believed to mediate this interaction. Disintegrins, such as echistatin [Sato et al. (1990), supra] and presumably contortrostatin, inhibit bone resorption by isolated osteoclasts; the mechanism of action is presumably by disrupting adhesion structures. Accordingly, compositions and methods for treatment of osteoporosis employing an amount of contortrostatin effective to inhibit bone resorption by osteoclasts are also contemplated as within the scope of the present invention.

Finally, contortrostatin has utility in the promotion of wound healing. Events involved in wound healing are known to include alterations in integrin expression or functional activity and suggest that integrin receptor modulation plays a central role in wound repair and inflammation. Fibronectin is also known to play a number of roles in the wound healing process. Although fibronectin function is thought to be critical to effective wound healing, there are reports that at least one of its activities (the binding of bacteria) may be counterproductive [Grinnell, F., J. Cell. Biochem. 26:107 (1984); Clark, R. A. F., Arch. Dermatol. 124:201 (1988)]; the presence of fibronectin in the wound bed may thus promote bacterial attachment and infection. Fibronectin also appears to be intimately involved in keloid formation. Keloids are a pathological consequence of wound healing that affects a significant proportion of non-caucasian patients. Keloids are benign tumors of connective tissue that grow beyond the boundary of the original wound and are rich in fibronectin and type I collagen [Sible, J. C. & Oliver, N., J. Cell. Biochem. Suppl. 16F:170 (1992)]. By virtue of their inhibition of cell-cell and cell-extracellular matrix interactions (including interaction with fibronectin), disintegrins such as contortrostatin would be expected to have a profound effect on processes involved in wound repair, including keloid formation.

A major problem following obstetrical and gynecological surgery is the formation of adhesions. This widespread phenomenon observed in peritoneal wound repair is a leading cause of pain, intestinal obstruction and infertility. Adhesion formation appears to involve an imbalance in the fibrinolytic and fibroproliferative inflammatory responses and may also involve a modulation of the cell-cell or cell-extracellular matrix interactions. There is strong evidence for an important role of fibrin during the initial stages of adhesion formation [diZerega, G. S., Prog. Clin. Biol. Res. 381:1 (1993)]. The presence of cellular elements, including platelets, further exacerbates the role of fibrin. In view of the role of platelets and fibrin in adhesion formation, the use of disintegrins such as contortrostatin as a potential therapeutic agent is most attractive.

In preliminary studies in a rabbit model of adhesion formation, abrasion and devascularization of the uterine horns of rabbits were employed to induce adhesion formation during wound healing in untreated animals [Rodgers, K. et al., *Int. J. Fertil.* 35:40 (1990)]. Alzet pumps were employed to continuously deliver contortrostatin at a rate of 10 μl/hr (36 μg/ml). In this model system, decreased adhesion formation was observed in treated animals compared to controls. Therefore, compositions and methods for preventing adhesion formation whereby an amount of contortrostatin effective to prevent adhesion formation is administered to a patient in need of such treatment are also contemplated as within the scope of the present invention.

As illustrated in the examples, contortrostatin may be isolated from the venom of *Agkistrodon contortrix contortrix* in a relatively straightforward manner. Alternatively, contortrostatin may also be prepared by exploiting a variety of biochemical methods in current use, such as recombinant DNA technology or the like. Thus, the purified protein may be partially sequenced (as is reported herein) and the sequence information used to deduce nucleotide sequences for making probes to identify the gene or genes that encodes a given protein. Once identified, the genes may be isolated and cloned into expression vectors. These vectors may be used to transform competent hosts to produce transformants that are capable of producing the snake venom protein.

Sources of DNA sequences encoding for the proteins include isolated DNA from suitable cells or cell lines, cloned DNA from a snake venom genomic library or cloned DNA from a messenger RNA library, where the total messenger RNA is reverse transcribed to DNA and cloned. Once a DNA sequence is identified which encodes for a protein of interest, the sequence of bases may be determined by known means [e.g., Maxam and Gilbert, *Proc. Natl. Acad. Sci. USA* 74:560 (1977)]. In addition, hybrid DNA technology may be employed for obtaining expression. The DNA sequence may be restriction mapped and appropriate sites for cleavage defined. In this way, the sequence may be excised and introduced into a vector having the appropriate regulatory signals. A more detailed discussion of suitable techniques for identification and expression of disintegrin genes is provided in, e.g., U.S. Pat. Nos. 5,182,260 and 5,196,403 to Maraganore et al., the entire disclosures of which are hereby incorporated by reference.

Further, the sequence encoding the native protein may then be manipulated (for example, by single or multiple mutations or deletions) in a manner well known in the art to provide modified proteins, in which changes of one or more amino acids have been introduced. Following the procedures described herein, the determination of whether a particular polypeptide exhibits an activity profile characteristic of contortrostatin would then be a matter of routine experimentation. Accordingly, the present invention contemplates both the native contortrostatin and mutations thereof which exhibit the characteristic activity profile defined herein. Moreover, contortrostatin may also be employed in the form of a fusion protein with a suitable thrombolytic agent. Fusion proteins of this type may be prepared in a manner analogous to that described for formation of platelet aggregation inhibitor/anti-thrombin polypeptide fusion proteins in the aforementioned U.S. Pat. Nos. 5,182,260 and 5,196,403 to Maraganore et al.

The compositions of the present invention comprise at a minimum an amount of contortrostatin effective to achieve the desired effect (i.e., prevent thrombus formation, prevent metastases in carcinoma patients, prevent adhesion formation, etc.) and a suitable carrier or excipient. In these compositions, contortrostatin is present in an amount sufficient to provide about 0.01 mg/kg to about 50 mg/kg per day, preferably about 0.1 mg/kg to about 5.0 mg/kg per day, and most preferably about 0.1 mg/kg to about 0.5 mg/kg per day. Such compositions have particular utility in the prevention of thrombus formation.

Alternatively, contortrostatin is administered in combination with at least one thrombolytic agent present in an amount effective to achieve thrombolysis. Suitable thrombolytic agents include, but are not limited to, the following: anisoylated plasminogen streptokinase activator complex (APSAC); tissue-type plasminogen activator (tPA); urokinase-type plasminogen activator (uPA); and fibrolase, a snake venom fibrinolytic agent as described in U.S. Pat. No. 4,610,879 to Markland, Jr. et al.

Contortrostatin may be administered by a variety of heretofore known means suitable for delivery thereof into the blood stream in substantial amounts. Intravenous administration of contortrostatin in a suitable liquid vehicle or excipient is presently contemplated as the preferred route of administration. Contortrostatin is soluble in water, and may therefore be effectively administered in a suitable aqueous solution (e.g., phosphate buffered saline). Alternatively, contortrostatin may be administered orally (in the form of tablets or capsules formulated with a suitable binder or excipient material, or in the form of aqueous or oily suspensions, solutions, emulsions, syrups or elixirs) or as a parenteral suspension. As is well known in the art, adjuvants such as local anesthetics, preservatives, buffering agents, lubricants, wetting agents, colorants, flavorings, fillers and diluents may suitably be included in any of these formulations.

The invention may be better understood with reference to the accompanying examples, which are intended for purposes of illustration only and should not in any sense be construed as limiting the scope of the invention as defined in the claims appended hereto.

EXAMPLES

Lyophilized venom from *Agkistrodon contortrix contortrix* was obtained from Biotoxins, Inc., St. Cloud, Fla. All chemicals were of the highest grade available. Pierce protein assay kit using bicinchoninic acid was employed to determine protein concentrations [Smith, P. K. et al., *Anal. Biochem.* 150:76 (1985)].

For hydrophobic interaction (HIC)-HPLC a Perkin Elmer 410 LC pump was employed with a LC-95 UV/VIS detector. For reverse phase HPLC a Spectra Physics LC 8810 pump was employed with an SP 8450 UV/VIS detector. Absorbance for HIC-HPLC was monitored at 280 nm and for RP-HPLC at 215 nm. A polypropyl aspartamide (250×21 mm) column (Poly LC, Columbia, Md.) was used for hydrophobic interaction HPLC. C18 (218TP54 and 218TP510) columns were used for reverse phase (RP) HPLC (Vydac, Hesperia, Calif.). For cation exchange chromatography a CM (carboxymethyl) 300 column (SynChrom, Inc., Lafayette, Ind.) was employed.

Example 1

Purification and Characterization of Contortrostatin

Contortrostatin was purified from *Agkistrodon contortrix contortrix* (Southern copperhead) venom using a four step HPLC procedure. For the first step of purification crude venom (1 g) was dissolved in 0.1M phosphate buffer containing 1M ammonium sulphate, pH 6.8 (buffer A) and applied to the polypropyl aspartamide HIC-HPLC column. Elution was achieved as follows: 50 minutes isocratically with 100% buffer A; a linear gradient for 90 minutes to 0.1M phosphate, pH 6.8 (buffer B); 40 minutes isocratic at 100% buffer B. Fractions of 10 ml were collected in a Pharmacia Frac 100 fraction collector at 4° C. using a flow rate of 5 ml/min. Fractions containing platelet aggregation inhibiting activity were pooled and concentrated by ultra-filtration using an Amicon stir cell with a YM3 membrane. Proteins were detected at 280 nm; platelet aggregation inhibiting activity was observed in the flow through.

Further purification was achieved by C18 RP-HPLC. Fractions containing platelet aggregation inhibiting activity were pooled and concentrated for this second step. The C18 column (218TP510) was equilibrated with 95% of 0.1% TFA in water (solvent A) and 5% of 80% acetonitrile in 0.1% TFA in water (solvent B). Elution was achieved as follows: isocratic at 95% solvent A and 5% solvent B for 10 minutes; a linear gradient to 40% solvent B in 65 minutes; linear gradient to 100% solvent B in 20 minutes; isocratic at 100% solvent B for 25 minutes. Fractions were collected manually every minute at a flow rate of 7 ml/minute. Contortrostatin eluted at 28% acetonitrile (66 minutes).

Fractions containing platelet aggregation inhibiting activity were pooled and rerun on the same C18 RP-HPLC column using a shallower gradient. Elution was achieved as follows: isocratic at 80% solvent A and 20% solvent B for 20 minutes; a linear gradient to 30% solvent B over 90 minutes; and a 25 minute linear gradient to 100% solvent B. Contortrostatin eluted as a sharp peak at 22% acetonitrile (82 minutes). The minor peak eluting just before contortrostatin also contained platelet aggregation inhibiting activity and had a similar molecular weight to that of contortrostatin; due to the low yield, this peak was not further characterized.

A final purification step was performed using pooled fractions from the previous step. These pooled fractions were applied to a cation exchange, CM300, HPLC column and elution was achieved by an increasing gradient of sodium chloride. Contortrostatin elutes at 52.5 minutes (160 mM NaCl). This step achieved a separation of contortrostatin from isoforms thereof. Yields of 1–2 mg of the four-step purified contortrostatin were obtained per gram of crude venom.

For SDS-polyacrylamide gel electrophoresis (SDS-PAGE) Tris-Tricine 16.5% gel was used according to published protocols under reducing and non-reducing conditions [Schagger, H. & Von Jagow, G., *Anal. Biochem.* 166:368 (1987)]. The gel was run using a BioRad minigel system and stained with silver [Morrisey, J. H., *Anal. Biochem.* 117:307 (1981)] or Coomassie blue R250.

SDS-PAGE analysis of contortrostatin revealed that it has a molecular mass of approximately 15,000 Daltons under non-reducing conditions and 5,000–7,000 Daltons under reducing conditions. This strongly suggests that contortrostatin is composed of two subunits. Another possibility, albeit unlikely, is that the large difference in migration may be attributed to differential uptake of SDS under non-reducing and reducing conditions.

The molecular weight of contortrostatin was confirmed by mass spectrometry using a triple quadrupole instrument with an electrospray ion source. A mass of 13,507 Daltons was determined for intact contortrostatin; the analysis also indicated a high degree of purity. Mass spectrometry of the reduced and pyridylethylated protein gave a mass of 7,996 Daltons. This is the expected value for the individual chains of a homodimer of this molecular weight, taking into account the incorporation of 1,248 mass units for the 12 pyridylethyl groups incorporated into the 6 reduced disulfide bounds (based on homology with known disintegrins, there should be 6 disulfide bonds). These findings place contortrostatin in a unique position among all the disintegrins reported to date in that it exists as a dimer. Scatchard analysis of contortrostatin binding to unactivated human platelets revealed a single class of binding sites with a dissociation constant ($K_d$) of 37 nM and number of binding sites ($B_m$) equal to 100,000. Reduction of the disulfide bonds completely eliminated platelet aggregation inhibitory activity, even at concentrations ten times the $IC_{50}$, suggesting that structural parameters are critical for maintaining activity.

Example 2

Assay of Platelet Aggregation Inhibitory Activity

Column fractions obtained during purification were assayed for activity using fresh human platelet rich plasma (PRP) prepared from blood obtained from human volunteers who had had no medication for at least two weeks. Blood (36 ml) was drawn into 4 ml of 0.1M citrate and centrifuged at 150×g for 20 minutes. The supernatant, PRP, was removed and the remaining blood was centrifuged at 10,000 RPM to obtain platelet poor plasma (PPP). Platelet counts were adjusted to 250,000 platelets/μl using a Coulter counter. A Helena four channel aggregometer was used to monitor platelet aggregation. Inhibition of ADP-induced platelet aggregation was monitored at 37° C. by adding venom fractions one minute prior to the addition of ADP (10–20 μM final concentration). Fractions exhibiting platelet aggregation inhibiting activity were pooled and further purified. Rabbit and canine PRP was prepared by the same procedure and used in the studies described below.

Contortrostatin inhibited ADP-induced platelet aggregation in human, canine, and rabbit PRPs (FIG. 1). Empty circles represent human platelet rich plasma, solid circles represent canine PRP, and empty triangles represent rabbit PRP. Varying concentration of contortrostatin were preincubated for one minute with PRP prior to the addition of ADP. Contortrostatin (0.73 μg/ml) inhibited 10 μM ADP-induced human platelet aggregation by 50% ($IC_{50}$). The $IC_{50}$ for 20 μM ADP-induced canine platelet aggregation was 1.8 μg/ml for contortrostatin. Interestingly, the $IC_{50}$ for contortrostatin mediated inhibition of rabbit platelet aggregation was considerably higher; the $IC_{50}$ for 20 μM ADP-induced rabbit platelet aggregation was 17.3 μg/ml for contortrostatin.

Example 3

Measurement of GPIIb/IIIa Specific Binding

Measurement of contortrostatin binding to platelet GPIIb/IIIa receptor was carried out using PRP prepared from blood obtained from human volunteers or male mongrel dogs. PRP was prepared as described above and the platelet count was determined with a H-10 cell counter (Texas International Laboratories, Inc., Houston, Tex.). PRP (180 μl) was incubated with 20 μl of varying concentrations of contortrostatin at room temperature. Radiolabelled antibody ($^{125}$I-7E3 IgG, 20 μl, 18 mg/ml, 80,000 cpm), specific for GPIIb/IIIa, was then added and the mixture incubated for 30 minutes. To establish equilibrium binding, 50 μl aliquots of the binding assay mixture were layered over 200 μl of 30% sucrose in 0.4 ml microcentrifuge tubes and spun at 10,000 RPM for 4 minutes in a swinging bucket rotor to separate platelet-bound antibody from free antibody. The pellet and the supernatant were separated and counted in a Packard Minaxi 5000 series gamma counter. The number of molecules of $^{125}$I-7E3 bound per platelet in the presence and absence of contortrostatin was calculated by using the following formula:

$$\frac{(4) \times 0.9 \text{ μg } 7E3 \times 3.76 \times 10^{12} \text{ molecules } 7E3/\text{μg}}{(5)}$$

wherein (1)=Pellet counts; (2)=Supernatant counts; (3)= Total CpM (1)+(2); (4)=Fraction bound (1)/(3); and (5)= Platelet counts per μl×45 μl.

Figure 2A:
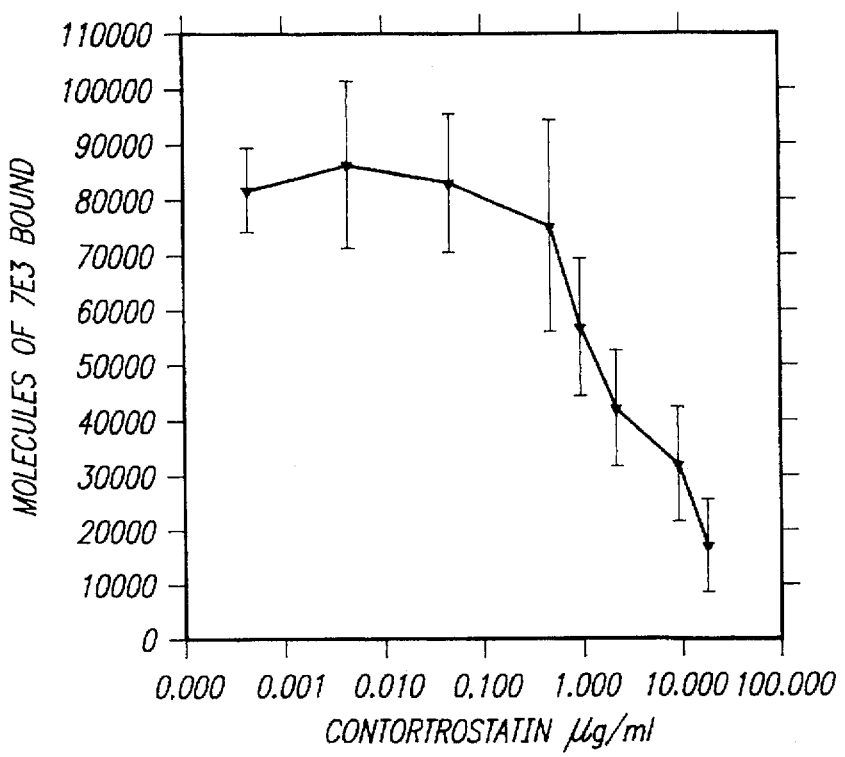
FIGS. 2A and 2B illustrate the results of binding studies of contortrostatin to human (FIG. 2A) and canine (FIG. 2B) GPIIb/IIIa in the presence of a fixed saturating concentration of murine monoclonal antibody 7E3.
Figure 2B:
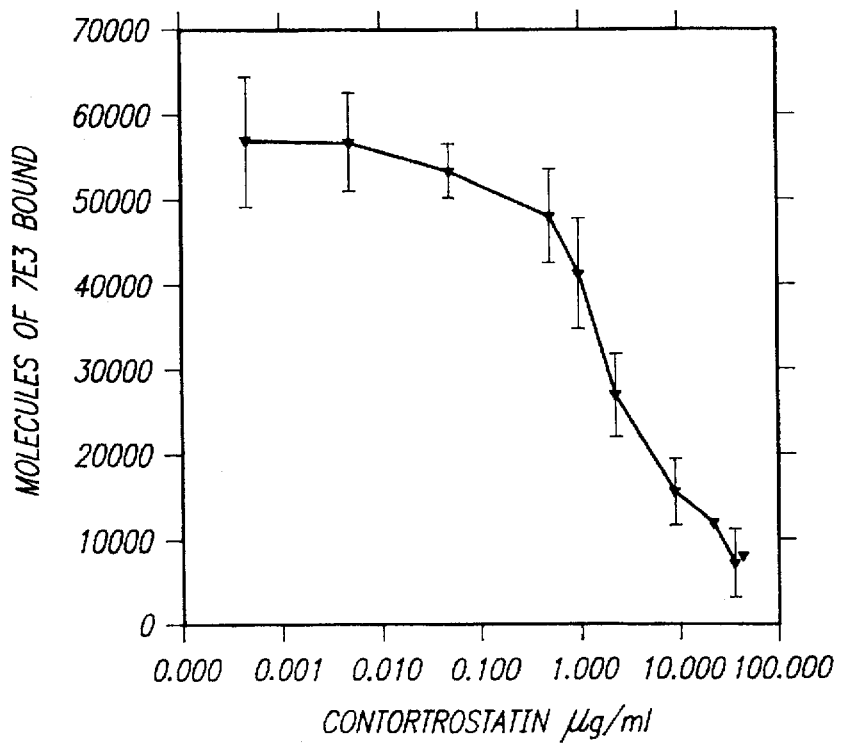

The competitive binding studies using 7E3 demonstrated specific platelet GPIIb/IIIa receptor binding for contortrostatin with both human (FIG. 2A) and canine (FIG. 2B) platelets. The concentration of contortrostatin to inhibit 50% of 7E3 binding to human GPIIb/IIIa ($IC_{50}$) is 0.4 μg/ml. The $IC_{50}$ for contortrostatin for canine GPIIb/IIIa is 0.24 μg/ml. These studies confirm that contortrostatin inhibits platelet aggregation by binding to GPIIb/IIIa.

Example 4

In Vivo Thrombolytic Efficacy of Contortrostatin

Contortrostatin has been studied in a reoccluding canine model of arterial thrombosis. The protein was studied initially by systemic infusion at different dosages to determine its relative potency. This data has permitted an assessment of the systemic dose needed for effective antithrombotic (antiplatelet) activity. The effects upon physiological parameters and circulating coagulation factors have also been monitored.

The model of carotid artery thrombosis in the anesthetized canine described is a modification of one developed for the study of experimentally-induced coronary artery thrombosis [Romson, J. L. et al., *Thromb. Res.* 17:841 (1980)]. The experimental procedure results in the formation of a platelet rich intravascular thrombus at the site of an electrolytically-induced endothelial lesion in proximity to a distal arterial stenosis. The carotid artery is selected for the experimental model, thereby allowing one vessel to be used as a control and the other to be used after administration of the thrombolytic and antithrombotic therapy. APSAC (anisoylated plasminogen streptokinase activator complex) has been used as the thrombolytic agent successfully in this model. The carotid artery response to the electrolytic injury is similar to that observed in the canine coronary artery but has the advantage of each dog demonstrating the ability to form bilateral occlusive thrombi. The lytic-antithrombotic combination of agents may then be administered to only one of the occluded vessels; this allows for an internal control and eliminates those animals that may not form thrombi due to causes unrelated to the vessel wall injury and subsequent occlusive thrombus formation, i.e., low circulating platelet counts, enhanced spontaneous thrombolysis, presence of heart worms, etc. Parameters which are recorded include repeated measures of: phasic and mean carotid artery blood flow velocity using an ultrasonic flow probe, time to thrombotic occlusion, time to recanalization, ex vivo platelet aggregation, prothrombin time, thrombin time, activated partial thromboplastin time, red cell and white cell counts, hematocrit, EKG profile and body temperature, before and after administration of APSAC or APSAC plus contortrostatin to separate groups of animals.

Figure 3:
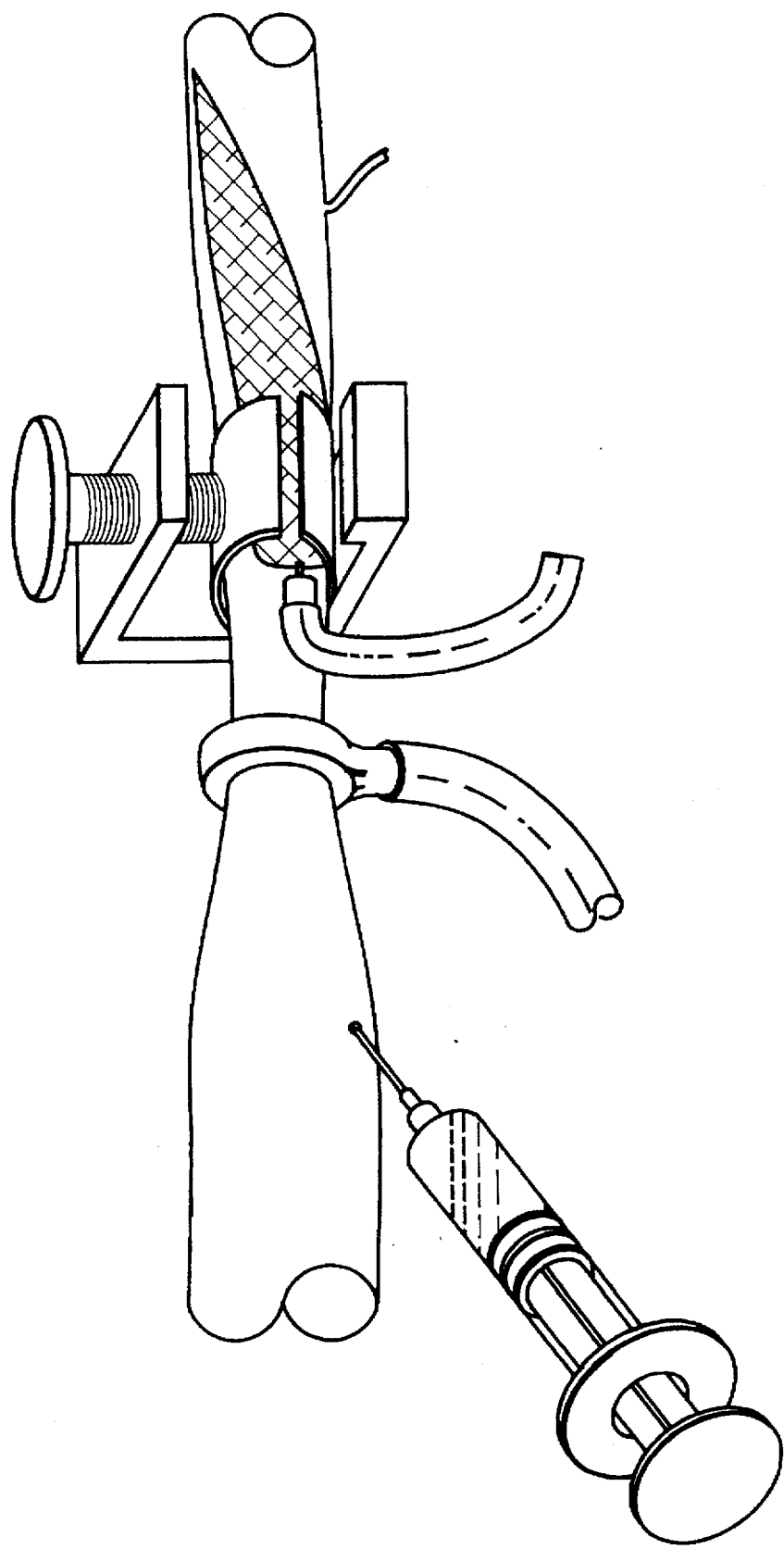
FIG. 3 is a schematic representation of an instrumented canine carotid artery showing placement of an ultrasonic flow probe, mechanical constrictor (stenosis) and intracarotid anodal electrode for inducing intimal injury to the vessel wall to initiate thrombus formation.

Conditioned male mongrel dogs (8–10 kg) have been used for all in vivo studies. Dogs are anesthetized with sodium pentobarbital, intubated and allowed to breath room air under positive pressure respiration. Arterial blood gasses and pH determinations are made every 45 minutes and appropriate adjustments made to maintain the blood gasses and arterial pH within normal limits. Both common carotid arteries and the right internal jugular vein are exposed. A catheter is inserted into the jugular vein for blood sampling and administration of the test drug. Arterial blood pressure is monitored from the cannulated femoral artery with the use of a blood pressure transducer. A Doppler flow probe is placed on each common carotid artery proximal to both the point of insertion of the intraarterial electrode and the mechanical constrictor. The constrictor is adjusted until the pulsatile flow pattern is reduced by 50% without altering mean blood flow. Blood flow velocity in the carotid vessels is monitored continuously. FIG. 3 is a schematic representation of the instrumentation of the carotid artery.

Electrolytic injury to the intimal surface of each carotid vessel is accomplished with the use of an intravascular electrode. Each intraarterial electrode is connected to the positive pole (anode) of a dual channel stimulator. The cathode is connected to a distant subcutaneous site. The current delivered to each vessel is monitored continuously and maintained at 300 μA. The anodal electrode is positioned to have the uninsulated portion in intimate contact with the endothelial surface of the vessel. Proper positioning of the electrodes in each of the carotid arteries is confirmed by visual inspection at the end of each experiment. The anodal current is applied for a maximum period of 3 hours or is terminated 30 minutes after blood flow in the involved vessel remains stable at zero flow velocity to verify having achieved formation of a stable occlusive thrombus. The right carotid artery serves as the control vessel, whereas the left carotid artery serves as the test vessel. Vessel wall injury is induced simultaneously in each carotid artery.

APSAC (0.05 U/kg) is infused as a bolus proximal to the thrombus in the left carotid artery only. The dose of APSAC has been determined as one that will consistently lyse the locally injected carotid thrombus without producing a systemic lytic effect. Thus, lysis in the uninjected right carotid should not occur. Contortrostatin is given intravenously in a 10% bolus immediately following APSAC and the remaining 90% is infused over 1 hour. Contortrostatin dosages ranged from 0.155 to 0.40 mg/kg; the agent was dissolved at the appropriate dose in a volume of 20 ml of sterile saline for infusion. Reperfusion is defined as the restoration of carotid artery blood flow velocity to 20% of baseline values. Patency is defined as measurable carotid artery flow velocity. Blood pressure, heart rate, and carotid artery flow velocity are monitored for 6 hours or until rethrombosis occurs.

Blood (20 ml) was withdrawn for platelet studies from the jugular cannula into a plastic syringe containing 3.2% sodium citrate as anticoagulant (1/10 citrate/blood, vol/vol). Blood was taken for platelet aggregation and whole blood cell counts at baseline 60, 120, 180, 240 and 300 minutes after the administration of contortrostatin. The platelet count was determined with a cell counter. Platelet rich plasma, the supernate present after centrifugation of anticoagulated whole blood at 140×g for 5 minutes, was diluted with platelet poor plasma to achieve a platelet count of 200,000/mm$^3$. Platelet poor plasma was prepared after the platelet rich plasma was removed, by centrifuging the remaining blood at 12,000×g for 10 minutes and discarding the bottom cellular layer. Ex vivo platelet aggregation was measured by established spectrophotometric methods with a four channel aggregometer by recording the increase in light transmission through a stirred suspension of platelet rich plasma maintained at 37° C. Aggregation was induced with arachidonic acid (0.65 mM and 0.325 mM) and ADP (20 µM and 5 µM). A subaggregatory dose of adrenaline (550 nM) was used to prime the platelets before stimulation. Values are expressed as percentage of aggregation, representing the percentage of light transmission standardized to platelet rich and platelet poor plasma samples yielding 0% and 100% of light transmission, respectively.

At the conclusion of the study protocol each vessel segment is ligated, proximal and distal to the point of injury, and removed without disturbing the intravascular thrombus. The vessel segment is opened and the intact thrombus is lifted off and weighed.

Figure 4:
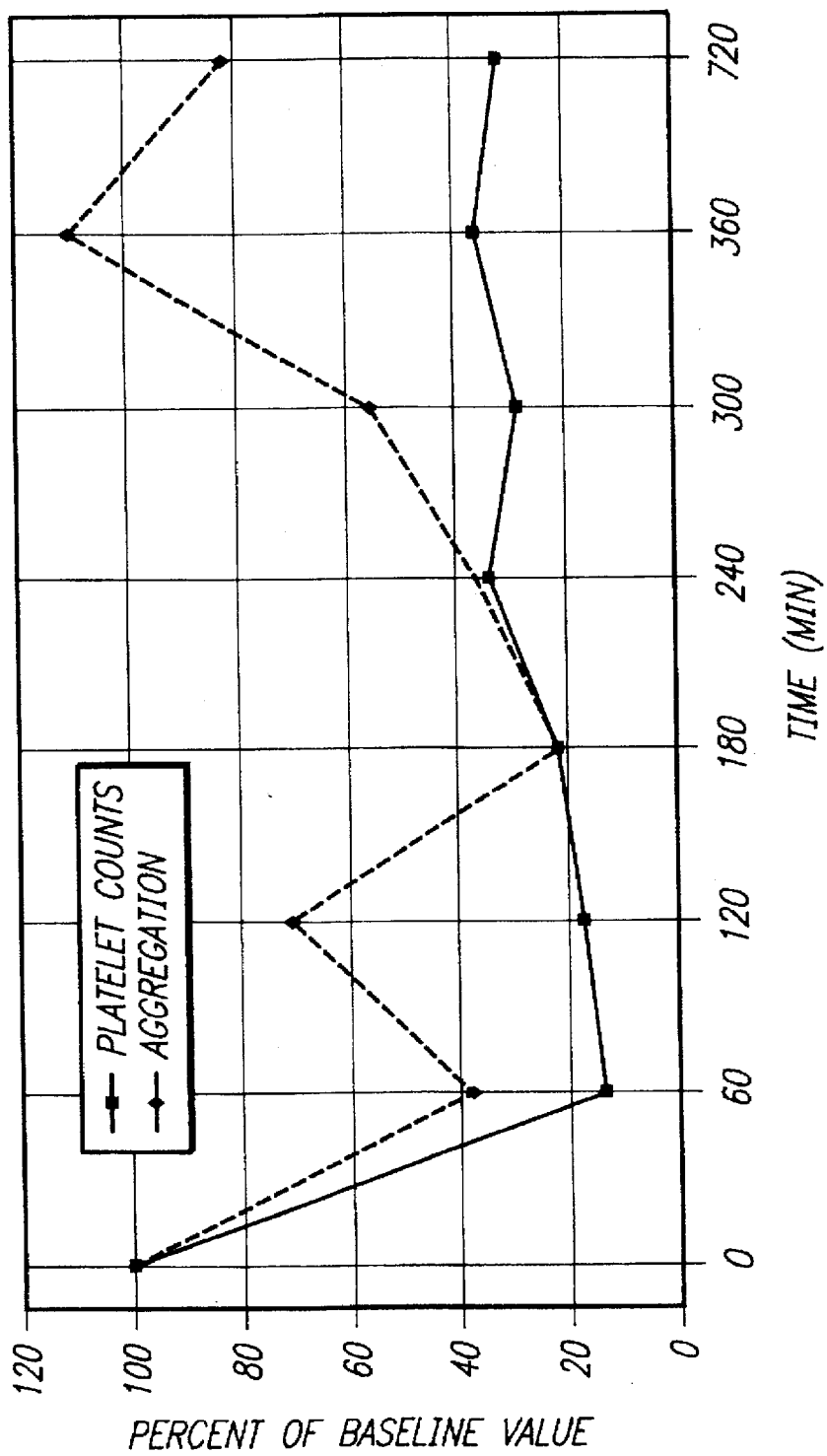
FIG. 4 illustrates platelet counts and platelet aggregability as percent of the value at zero time in a canine treated with anisoylated plasminogen streptokinase activator complex (APSAC) and contortrostatin.

Five animals have been studied thus far with contortrostatin plus APSAC, six with APSAC alone, and a positive control group of six dogs with APSAC plus 7E3 anti-GPIIb/IIIa monoclonal antibody, There were essentially no changes in mean arterial blood pressure or mean heart rate following infusion of contortrostatin. Further, the carotid artery flow velocity stayed at a high level following infusion of APSAC plus contortrostatin as compared to APSAC infusion alone. In the group of animals infused with APSAC alone, the carotid artery opened for a few minutes following infusion of the lytic agent but then reoccluded and remained closed for the duration of the study. In the positive control group, the animals were infused with APSAC (0.1 U/kg) intraarterially and this was followed by a bolus of 7E3 anti-GPIIb/IIIa F(ab')2 (0.8 mg/kg). In these three animals, the carotid artery remained open following infusion of the combination of APSAC and 7E3 and remained open until the conclusion of the experimental protocol. In the group of five animals infused with APSAC plus contortrostatin the results were essentially the same as with the combination of 7E3 and APSAC. However, Table 1 reveals that there was a significant advantage to the combination of APSAC plus contortrostatin in terms of the residual thrombus weight. In Table 1, CTTX=contortrostatin and RCA=right carotid artery. In the group of five animals treated with this combination of agents the residual thrombus weight per kg dog weight was 1.5, versus 2.4 in the six animals in the APSAC plus 7E3 group, and 4.1 in the APSAC alone group (six animals). Finally, in one of the dogs treated with APSAC plus contortrostatin (0.155 mg/kg) platelet aggregation and platelet counts were followed (FIG. 4); contortrostatin infusion began at time 0 and was continued for 60 minutes thereafter. These results are typical of those in dogs in this group. It can be seen that platelet aggregation was compromised by treatment with the venom protein, but that there appeared to be a return of aggregation at the conclusion of the experiment. Similarly, the platelet count was also depressed during the course of the experiment. It is suspected that the platelets are sequestered in some sanctuary such as the spleen and are then released following a short residence time; platelets returning into the circulation appear to be functional. There is a drop in platelet counts to 10-20% of the baseline value, with recovery to 30-40% by the conclusion of the experimental procedure. Platelet aggregability fluctuates somewhat due to the low platelet count; however, it can be seen that platelet aggregability in the residual platelets appears to be returning to normal at the conclusion of the experimental procedure.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

TABLE 1

WEIGHT OF RESIDUAL THROMBUS IN CANINE CAROTID ARTERY THROMBOSIS MODEL

| Dog # | APSAC Control | | APSAC & 7E3 | | APSAC & CTTX | |
|---|---|---|---|---|---|---|
| | Dog Weight (kg) | RCA Thrombus (mg) | Dog Weight (kg) | RCA Thrombus (mg) | Dog Weight (kg) | RCA Thrombus (mg) |
| 1 | 19.2 | 27.3 | 9.4 | 37.3 | 15.2 | 16.8 |
| 2 | 6.5 | 47.6 | 12.2 | 37.5 | 8.2 | 19.2 |
| 3 | 18.2 | 90.5 | 17 | 53.2 | 9.2 | 3.5 |
| 4 | 20.2 | 60.1 | 11.6 | 3.2 | 8.5 | 33.1 |
| 5 | 16.8 | 67.5 | 8.6 | 36.5 | 9 | 15.1 |
| 6 | 10 | 78.5 | 15.9 | 11.8 | | |
| Mean | 15.2 | 61.9 | 12.5 | 29.9 | 10 | 14.6 |
| SEM | 2.1 | 8.4 | 1.4 | 7.6 | 1.4 | 4.9 |
| Thrombus weight per kg | | 4.1 | | 2.4 | | 1.5 |

What is claimed is:

1. In a method of treating thrombotic disease wherein at least one thrombolytic agent is administered in an amount effective to lyse thrombi, the improvement comprising administering to a patient in need of such treatment contortrostatin in an amount effective to prevent thrombus formation.

2. A method according to claim 1, wherein contortrostatin is administered in an amount within the range of about 0.01 mg/kg to about 50 mg/kg per day.

3. A method according to claim 1, wherein contortrostatin is administered in an amount within the range of about 0.1 mg/kg to about 5 mg/kg per day.

4. A method according to claim 1, wherein contortrostatin is administered in an amount within the range of about 0.1 mg/kg to about 0.5 mg/kg per day.

5. A method according to claim 1, wherein said thrombolytic agent is selected from the group consisting of anisoylated plasminogen streptokinase activator complex, tissue-type plasminogen activator, urokinase-type plasminogen activator and fibrolase.

6. A composition for treatment of thrombotic disease in a mammal, comprising contortrostatin in an amount effective to prevent thrombus formation and a suitable carrier or excipient.

7. A composition for treatment of thrombotic disease in a mammal, comprising contortrostatin in an amount effective to prevent thrombus formation, at least one thrombolytic agent in an amount effective to lyse thrombi and a suitable carrier or excipient.

8. A composition according to claim 6, wherein said thrombolytic agent is selected from the group consisting of anisoylated plasminogen streptokinase activator complex, tissue-type plasminogen activator, urokinase-type plasminogen activator and fibrolase.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Asp Pro Glu Asn Pro Cys Cys Asp Ala Thr Cys Lys Leu Arg Thr Gly
1               5                   10                  15

Ser Gln Cys Ala Glu Gly Leu Cys Xaa Asp Gln Cys Xaa Phe Met Lys
            20                  25              30

Glu Cys Gly Glu Gly Gly Xaa Val Xaa Xaa Gly Asp Xaa
            35              40              45
```